(12) United States Patent
Blouquin et al.

(10) Patent No.: US 7,976,869 B2
(45) Date of Patent: Jul. 12, 2011

(54) FENOFIBRATE TABLETS

(75) Inventors: Pascale Blouquin, Talant (FR); Philippe Reginault, Fontaine les Dijon (FR)

(73) Assignee: Laboratoires Fournier S.A., Dijon (FR)

( * ) Notice: Subject to any disclaimer, the term of this patent is extended or adjusted under 35 U.S.C. 154(b) by 101 days.

(21) Appl. No.: 12/603,341

(22) Filed: Oct. 21, 2009

(65) Prior Publication Data

US 2010/0040682 A1 Feb. 18, 2010

Related U.S. Application Data

(63) Continuation of application No. 10/466,962, filed as application No. PCT/FR02/00245 on Jan. 22, 2002, now abandoned.

(30) Foreign Application Priority Data

Jan. 22, 2001 (FR) ..................................... 01 00833

(51) Int. Cl.
*A61K 9/20* (2006.01)
*A61K 9/28* (2006.01)
*A61K 9/14* (2006.01)

(52) U.S. Cl. ......... 424/465; 424/464; 424/474; 424/489

(58) Field of Classification Search .................. None
See application file for complete search history.

(56) References Cited

U.S. PATENT DOCUMENTS

| | | | | |
|---|---|---|---|---|
| 4,895,726 A * | 1/1990 | Curtet et al. | ................... | 424/456 |
| 5,776,495 A | 7/1998 | Duclos et al. | | |
| 5,827,536 A | 10/1998 | Laruelle | | |
| 6,042,847 A * | 3/2000 | Kerc et al. | ..................... | 424/472 |
| 6,074,670 A | 6/2000 | Stamm et al. | | |
| 6,277,405 B1 * | 8/2001 | Stamm et al. | .................. | 424/462 |
| 7,101,574 B1 * | 9/2006 | Criere et al. | ................... | 424/489 |

FOREIGN PATENT DOCUMENTS

| | | |
|---|---|---|
| CA | 2 253 769 A1 | 11/1999 |
| CA | 2 270 306 A1 | 11/1999 |
| EP | 0 793 958 | 9/1997 |
| EP | 0 904 781 | 3/1999 |
| EP | FR 2 783 421 | 1/2003 |
| FR | 2 494 112 | 5/1982 |
| WO | WO 98/31361 | 7/1998 |
| WO | WO 00/30615 | 6/2000 |
| WO | WO 00/57918 | 10/2000 |

OTHER PUBLICATIONS

Balfour et al. "Fenofibrate: a review of its pharmacodynamic and pharmacokinetic properties and therapeutic use in dyslipidaemia". *Drugs*, vol. 40, No. 2, pp. 260-290 (1990).

Guichard et al. "Demonstration of kinetic bioequivalence between lipanthyl 200 M and lipanthyl 300". *Journal International de Medicine*, vol. 206, pp. 48-50 (1991).

Gaunt et al. "Short-term toxicity of diethylene glycol monoethyl ether in the rat, mouse, and pig". *Food, Cosmet., Toxicology*, vol. 6, pp. 689-705 (1968).

Budden et al. *Drug Research*, vol. 28, No. II, pp. 1571-1579 (1978) and English abstract.

Kimmel. "Reproductive and development effects on diethylene and triethylene glycol (methyl-, ethyl-) ethers". *Occupational Hygiene*, vol. 2, pp. 131-151 (1996).

Ben-Amor et al. Proceedings of the 5th Congressional International Technol. Pharmacology, vol. 3, pp. 190-199 (1989) and English abstract.

* cited by examiner

*Primary Examiner* — Humera Sheikh
(74) *Attorney, Agent, or Firm* — Merchant & Gould P.C.

(57) ABSTRACT

The present invention relates to a novel galenic formulation of fenofibrate for oral administration and to the process for its preparation. According to the invention, the formulation is a tablet obtained by compressing a mixture comprising:

a) granules containing:

1 to 5% of a surfactant;

micronized fenofibrate; and at least one solid excipient selected from starch, cellulose and derivatives thereof, with the exception of C12 disaccharides, said granules being obtained by granulating the mixture with the aid of an aqueous solution of polyvinylpyrrolidone;

b) crosslinked polyvinylpyrrolidone; and c) optionally flow aids or lubricants, the amount of fenofibrate being greater than 50% by weight, expressed relative to the weight of the tablet.

21 Claims, No Drawings

FENOFIBRATE TABLETS

This application is a Continuation Application of U.S. application Ser. No. 10/466,962, filed Oct. 16, 2003, which is a National Stage Application of PCT/FR2002/000245, filed Jan. 22, 2002, which claims the benefit of Serial No. 01/000833, filed Jan. 22, 2001 in France and which applications are incorporated herein by reference. A claim of priority to all, to the extent appropriate is made.

The present invention relates to a novel galenic formulation of fenofibrate for oral administration, to the process for its preparation and to the drugs manufactured from these formulations.

Fenofibrate (INN), which belongs to the fibrate family, has been known for many years as a medicinal active principle because of its efficacy in lowering the blood triglyceride and cholesterol levels. Thus fenofibrate is widely prescribed in numerous countries when there is a need to reduce the risk of atherogenesis.

It is also known that, to obtain a satisfactory hypocholesterolemic effect, it is desirable to maintain a circulating level of fenofibric acid (which is the active metabolite of fenofibrate) in the order of 6 to 10 mg/l. Such a level is obtained in particular with a unit dose of fenofibrate of 300 mg in gelatin capsule form (cf. Drugs 40 (2) pp 260-290 (1990)).

It is also known that substantial variations in the circulating levels exist according to the pathological conditions observed in patients. In general terms, for all drugs, it is preferable to maintain a circulating level of active metabolite that is necessary to obtain the desired therapeutic effect, while at the same time making the patient absorb the minimum amount of active principle. It is for this reason that formulations are sought which offer the highest possible bioavailability so as to optimize the dosage and limit any side effects of the active principle.

Taking these factors into account, it is seen that the galenic formulation of an active principle absorbed by the oral route is of great importance in obtaining the therapeutic effect under optimum conditions.

Fenofibrate was marketed originally in the form of gelatin capsules containing a 100 mg dose of active principle, with a dosage of 3 capsules a day, and then in the form of gelatin capsules containing a 300 mg dose of active principle, prescribed with a dosage of one capsule a day. According to the studies mentioned above, after the administration of a gelatin capsule containing a 300 mg dose to healthy volunteers, the maximum circulating level of fenofibric acid is about 6 to 9 mg/l and the area under the curve is 145 to 170 mg/l.h.

Another formulation, disclosed in patent document EP 330 532 and marketed in France under the mark LIPANTHYL® 200M, results from a process that consists in comicronizing the fenofibrate with a solid surface-active compound to give an intimate and finely divided mixture of the two products. This type of formulation enables the dosage to be reduced to 200 mg/day in a single dose to give plasma fenofibric acid concentrations that are very close to those obtained with a 300 mg dose of non-comicronized fenofibrate (Journal International de Médecine (1991) no. 206, pp 48-50). This formulation offers approximately a 30% improvement in bioavailability compared with the original formulation.

Patent document FR 2 494 112 proposes another type of formulation, namely microgranules in which a neutral core, consisting of sucrose and starch, is coated with micronized fenofibrate and then covered with a microporous protective layer. The recommended dosage in this case is 250 mg/day, which corresponds to an intermediate bioavailability compared with the previous formulations.

Also, patent document EP 757 911 discloses a process for the preparation of a fenofibrate formulation which consists in making up a solution of the active principle in diethylene glycol monoethyl ether and packaging this solution in soft capsules. According to the results mentioned in said document, the administration of 100 mg/day of fenofibrate affords the plasma fenofibric acid concentrations required to ensure the efficacy of the drug. In other words, this formulation has twice the bioavailability of the formulation described in patent document EP 330 532. However, such a formulation throws up the problem that results from the oral administration of a relatively large amount of solvent. In fact, depending on the formulations described, the administration of 100 mg of fenofibrate corresponds to the simultaneous administration of 1500 mg of a diethylene glycol ether. Now, as fenofibrate is a hypolipidemic intended for prescription over prolonged periods, the use of such a formulation would amount to the regular daily absorption by the patient of 1.5 g of a diethylene glycol ether, the biological effects of which are not totally neutral (cf. Food Cosmet. Toxicol. (1968) 6 (6) pp 689-705; Arzneim. Forsch. (1978) 28(9) pp 1571-1579; Occup. Hyg. (1996) 2 (1-6, Proceedings of the Int. Symposium on Health Hazards of Glycol Ethers, 1994) 131-151).

Patent document WO 00/57918 also proposes a fenofibrate formulation in solution in the form of a preconcentrate that is intended to form an emulsion in the presence of an aqueous phase, i.e. in the patient's stomach after administration. However, this type of formulation requires the use of leaktight capsules resistant to the oily substance.

Patent document WO 00/30615 also proposes a liquid fenofibrate formulation consisting of micronized particles of fenofibrate held in suspension in a liquid in the presence of surfactants.

Also, $5^{ème}$ Congrès Intern. Technol. Pharm. Vol. 3 (1989) pp 190-199 discloses a formulation in the form of a solution of fenofibrate in dimethyl isosorbide mixed with a dispersant. According to the tests mentioned, the bioavailability obtained is essentially much less dependent on the presence of food in the gastric medium, which already represents an advance relative to the conventional gelatin capsule form, for which the bioavailability is said to vary from 26% on an empty stomach to 89% after a meal.

A formulation similar to the previous one is proposed in patent document EP 904 781, which recommends preparing a co-melt of fenofibrate and a solid dispersant such as croscarmellose or polyvinylpyrrolidone.

According to patent document CA 2 253 769, the fenofibrate is formulated in the form of a coprecipitate with a water-soluble excipient such as, in particular, hydroxypropyl methyl cellulose. However, the process for the manufacture of such a coprecipitate requires the use of organic solvents, which have to be completely removed from the finished product and which also present safety problems during drying by atomization. A formulation similar to this is described in patent document EP 761 208.

Also, patent document CA 2 270 306 discloses gelatin capsules or tablets containing fenofibrate comicronized with lactose, for which the bioavailability of the active principle is improved by comparison with a formulation in which the fenofibrate is micronized on its own and then mixed with lactose.

Other dry gelatin capsule forms of fenofibrate have also been described, for example in patent document EP 793 958, which proposes mixing the fenofibrate with PVP (polyvinylpyrrolidone), crosslinked PVP and optionally other excipients, granulating the resulting mixture with a solution of a surfactant and then drying the granules and packaging them in gelatin capsules, or in patent document FR 2 783 421, which, in a process very similar to the previous one, recommends micronizing the fenofibrate, granulating it in the presence of a liquid medium comprising a surfactant, water and a water-miscible alcohol and then drying the resulting granules, which can subsequently be mixed with other excipients and then packaged in gelatin capsules.

Furthermore, patent document FR 2 758 459 discloses a composition in the form of granules or tablets in which the fenofibrate, in micronized form, is associated with a hydrophilic polymer (especially polyvinylpyrrolidone) and optionally with a surfactant. The results obtained with granules corresponding to this formulation containing a surfactant show a more rapid dissolution of the fenofibrate in laboratory tests. A comparative pharmacokinetic study also shows an improved bioavailability, especially when considering the parameters of plasma fenofibric acid concentration and area under the curve.

This last formulation can be presented in the form of tablets, but in this case the tablets that result have a unit weight of about 750 mg for a 160 mg dose of fenofibrate. Because of their relatively large size, such tablets are difficult to administer and are thus of limited value.

It is known in general that the tablet form is more advantageous than the gelatin capsule form insofar as:
on the one hand, weight for weight, a tablet is smaller than a gelatin capsule; and
on the other hand, the industrial production rates are higher for tablets than for gelatin capsule forms or soft capsule forms.

In addition, the tablet form avoids the use of raw materials of animal origin, such as gelatin, which is the essential constituent of gelatin capsules.

Under these conditions the object of the present invention is to solve the technical problem that consists in the provision of a novel fenofibrate formulation which has a good bioavailability and which makes it possible to produce tablets of reduced size which are easier to administer than those described in the state of the art, especially in patent document FR 2 758 459.

It was sought more particularly to provide a formulation containing a reduced amount of excipients while remaining suitable for forming tablets which can be produced on the industrial scale and which have good crushing strength and friability characteristics together with a good bioavailability.

It was thus discovered that it was possible to achieve this objective and, contrary to the teaching of the prior art, to obtain tablets which contain more than 50% by weight of active principle and whose bioavailability is equivalent to that of commercial gelatin capsules containing a comicronizate of fenofibrate and a solid surfactant.

Thus, according to a first feature, the invention relates to a pharmaceutical composition in the form of a tablet for oral administration which can be obtained by compressing a mixture comprising:
a) granules containing:
 1 to 5% of a surfactant;
 micronized fenofibrate; and
 at least one solid excipient selected from starch, cellulose and derivatives thereof, with the exception of $C_{12}$ disaccharides,
 said granules being obtained by granulating the mixture with the aid of an aqueous solution of polyvinylpyrrolidone;
b) crosslinked polyvinylpyrrolidone; and
c) optionally flow aids or lubricants,
the amount of fenofibrate being greater than 50% by weight, expressed relative to the weight of the tablet.

Such a formulation makes it possible to solve the aforementioned technical problem in a particularly advantageous manner since it affords tablets which can be produced industrially, which have excellent crushing strength and friability characteristics and which are sufficiently small to be acceptable to patients, which is particularly important in the context of a long-term hypocholesterolemic treatment. Furthermore, the tablets obtained unexpectedly show an equivalent bioavailability to that of gelatin capsules containing the active principle in the form of a comicronizate with the surfactant.

In one preferred embodiment of the invention, the aforementioned surfactant is solid and takes the form of a comicronizate with the fenofibrate.

In another preferred embodiment of the invention, the aforementioned surfactant is introduced into the granules in the granulating solution with the polyvinylpyrrolidone.

According to one particular characteristic of the invention, the tablet contains between 50 and 250 mg of fenofibrate.

According to another particular characteristic of the invention, the aforementioned solid surfactant is sodium laurylsulfate.

According to another particular characteristic, one of the aforementioned solid excipients is pregelatinized starch, which is present in an amount of 15 to 40% of the weight of the fenofibrate.

According to yet another particular characteristic, one of the excipients is microcrystalline cellulose, which is present in an amount of 5 to 30% of the weight of the fenofibrate.

In another, currently preferred embodiment of the invention, the aforementioned tablet has a coating consisting of a film of varnish for protection against moisture, preferably based on a water-dispersible polymer.

According to a second feature, the invention relates to a process for the preparation of a pharmaceutical fenofibrate composition in the form of a tablet for oral administration, as described above.

In a first embodiment, this process is essentially characterized in that it comprises:
the comicronization of an effective amount of fenofibrate and a solid surfactant, which is used in an amount of between 1 and 5% by weight, based on the weight of fenofibrate;
the mixing, in the form of powders, of the resulting product with at least one solid excipient selected from starch, cellulose and derivatives thereof, with the exception of $C_{12}$ disaccharides;
the granulation of the resulting mixture of powders with the aid of an aqueous solution of polyvinylpyrrolidone;
the mixing of the resulting granules with crosslinked polyvinylpyrrolidone and optionally flow aids or lubricants, it being specified that the amount of fenofibrate is greater than 50% by weight, expressed relative to the weight of the tablet;
the compression of the mixture produced; and
optionally the film-coating of the resulting tablet with a protective varnish, preferably based on a water-dispersible polymer.

In a second embodiment, this process is essentially characterized in that it comprises:
the mixing, in the form of powders, of micronized fenofibrate with at least one solid excipient selected from starch, cellulose and derivatives thereof, with the exception of $C_{12}$ disaccharides;
the granulation of the resulting mixture of powders with the aid of an aqueous solution of polyvinylpyrrolidone and a surfactant, said surfactant being in an amount of between 1 and 5% by weight, based on the weight of fenofibrate;

the mixing of the resulting granules with crosslinked polyvinylpyrrolidone and optionally flow aids or lubricants, it being specified that the amount of fenofibrate is greater than 50% by weight, expressed relative to the weight of the tablet;

the compression of the mixture produced; and optionally the film-coating of the resulting tablet with a protective varnish, preferably based on a water-dispersible polymer.

DETAILED DESCRIPTION

The invention therefore proposes a novel galenic form of fenofibrate for oral administration in the form of a tablet, as defined above, said tablet form being obtained by the compression of a novel formulation.

This formulation, consisting of the aforementioned granules mixed with crosslinked polyvinylpyrrolidone, has a good compressibility and makes it possible in a particularly novel manner to obtain tablets of reduced size containing more than 50% by weight of active principle. Thus it is possible according to the invention to produce a tablet with a unit weight of less than 400 mg for a 200 mg dose of fenofibrate in a single administration.

According to the invention, the fenofibrate is first micronized on its own or comicronized with a solid surfactant to give a powder whose mean particle size is preferably less than 30 μm and particularly preferably less than 10 μm. More precisely, in the case of comicronization, the crystalline fenofibrate and the powdered solid surfactant are mixed and the mixture is then ground in a micronizer, for example according to the technology described in patent document EP 330 532, thereby making it possible to obtain an intimate mixture of the two constituents and substantially to improve the bioavailability of the fenofibrate. The fenofibrate or the fenofibrate/surfactant mixture is advantageously micronized in an air jet micronizer, which makes it possible to obtain a powder with a mean particle size in the order of 5 to 10 μm without heating the products.

In the case of comicronization of the fenofibrate/surfactant mixture, the amount of solid surfactant is in the order of 1 to 5% of the amount of fenofibrate, preferably in the order of 3 to 4%. In practice, an ionic or non-ionic solid surfactant is chosen. Among the surfactants which can be used, sodium laurylsulfate is preferred. The comicronized fenofibrate and surfactant are then mixed with at least one pulverulent excipient and the mixture is granulated, preferably with the aid of an aqueous solution of polyvinylpyrrolidone.

When using fenofibrate micronized on its own, the latter is mixed with at least one pulverulent excipient, and the surfactant (also used in an amount in the order of 1 to 5% by weight, expressed relative to the weight of fenofibrate) is preferably introduced with the polyvinylpyrrolidone in aqueous solution, i.e. with the granulating liquid. This mode of preparation is applied especially in the case of a liquid or viscous surfactant, for example polysorbates or medium-chain fatty acid esters.

Among the pulverulent excipients which can be used within the framework of the invention, preference is given to starch and/or cellulose or derivatives thereof, for example carboxymethyl cellulose, with the exception of $C_{12}$ disaccharides. Pregelatinized starch, which is a good disintegrating agent, and microcrystalline cellulose, which makes it possible to obtain a good cohesion and reduce the risks of the tablet splitting, are particularly preferred.

Contrary to the teaching of the closest prior art, the tablet according to the invention does not contain $C_{12}$ disaccharides, particularly lactose, which is often present in the known tablet formulations. It has unexpectedly been discovered that, in the case of a tablet based on fenofibrate, replacing the lactose with appropriately chosen pulverulent excipients makes it possible to improve the bioavailability of the active principle while at the same time substantially reducing the amount of excipients required, and thereby to obtain a smaller tablet, which is very advantageous.

Preferably, these excipients are added in a total amount corresponding to about 30 to 70% and preferably 45 to 55% of the weight of fenofibrate, each of the excipients, considered independently, being present in an amount of between 5 and 40% and preferably of between 10 and 35% by weight, relative to the weight of fenofibrate.

The pulverulent mixture consisting of the fenofibrate and the aforementioned excipients is granulated, for example in a paddle mixer or any other apparatus suitable for producing granules, by means of a binding solution advantageously comprising polyvinylpyrrolidone in water. This granulation is preferably carried out using a polyvinylpyrrolidone with an average molecular weight of between 25,000 and 100,000. The granules obtained are then sized by passage through a grid with a mesh size advantageously of 1 to 2.5 mm, after which they are dried, preferably in a fluidized bed granulating dryer.

The dry granules obtained can then be mixed with a solid external phase consisting of formulating agents such as lubricants, flow aids, binders or disintegrating agents. Among these agents, preference is given to crosslinked polyvinylpyrrolidone, which accelerates the disintegration of the tablet in aqueous media, and/or magnesium stearate, which lubricates the mixture.

The excipients constituting the external phase of the granules are generally present in an amount corresponding to about 5 to 25% and preferably of 8 to 15% of the weight of fenofibrate.

In one preferred embodiment of the invention, the external phase comprises crosslinked polyvinylpyrrolidone as the disintegrating agent, advantageously in an amount of 6 to 18% and preferably of 10 to 14% by weight, based on the weight of fenofibrate.

In general, the crosslinked polyvinylpyrrolidone, also known as crospovidone, has a branched polymer network with molecular weights in excess of 1,000,000.

The mixture of granules and these excipients is advantageously homogenized, for example in a horizontal or vertical paddle mixer. The resulting mixture is then converted to tablets sized so that each tablet contains 50 to 250 mg of fenofibrate and thus weighs between about 100 and 500 mg. The compression operation is carried out on an alternating or, preferably, rotary machine equipped with dies having a diameter in the order of 5 to 12 mm and preferably of 8 to 10 mm so as to produce small tablets.

The resulting tablets can be used directly in therapeutics but, in view of the hydrophilic character of certain excipients, the tablets are preferably coated with a protective varnish, preferably based on water-dispersible polymers, in order to preserve the drug better. Nevertheless, this film-coating is not essential and the tablet can be preserved well by other means, for example by a packaging that limits the exchanges of water vapor with the outside. The film-coating can be carried out in conventional manner by processes known to those skilled in the art, for example by spraying a solution of film-forming polymer onto the tablets placed in a turbine. This film-coating also makes it possible, if appropriate, to color the tablets by adding a colored pigment to the solution of film-coating polymer.

The following Preparative Example, together with the results obtained from clinical studies, will provide a clearer assessment of the subject of the invention.

Example 1 a) Preparation of the Comicronizate of Fenofibrate 6.8 kg of crystalline fenofibrate and 238 g of sodium laurylsulfate are mixed in a horizontal paddle mixer for 6 min and this homogeneous mixture is then finely ground in an air jet micronizer to give a comicronizate with a mean particle size in the order of 5 to 10 µm.

b) Preparation of the Internal-Phase Granules 7.038 kg of the comicronizate obtained according to the above preparation, 2.312 kg of pregelatinized starch (reference LYCATAB® PGS, marketed by ROQUETTE) and 1.190 kg of microcrystalline cellulose (reference AVICEL® PH 102 from FMC Corp.) are charged into a horizontal paddle mixer (LÖDIGE) and these powders are mixed for 3 minutes. The mixture is then granulated in the mixer by spraying with a polyvinylpyrrolidone solution obtained from 357 g of PVP (reference Kollidon K30, marketed by BASF) and 3.625 l of purified water. The resulting granules are sized by passage over an oscillating granulator (ERWEKA) equipped with a grid having a mesh size of 2.5 mm. The sieved granules are then transferred to a fluidized bed dryer and dried by the passage of air at 50-60° C.

c) Preparation of the Mixture for Compression 10.897 kg of the granules obtained by the above process, 833 g of crosslinked polyvinylpyrrolidone (reference POLYPLASDONE® XL 10, marketed by GAF) and 170 g of magnesium stearate are mixed in a horizontal paddle mixer (LÖDIGE) for 6 to 10 minutes. This gives the granules mixed with the external phase and ready for compression.

d) Preparation of the Tablets

The mixture obtained above is compressed in a rotary machine equipped with six 10R10 die stations. The machine is adjusted to produce tablets with a unit weight of 350 mg, which corresponds to a 200 mg dose of fenofibrate per tablet. The tablets obtained have a hardness of about 89 N.

e) Film-Coating

The tablets obtained according to the above operation are placed in a stainless steel turbine (ERWEKA) equipped with a spray gun, a hot-air blower and a suction system. The rotation of the turbine is set to 16 rpm and a solution of 75 g of film-forming polymer (reference OPADRY OYS®, marketed by COLORCON) in 1.425 kg of 80% ethanol is sprayed in. The spraying lasts about 2 hours. The film-coated tablets obtained are then cooled and packaged. Each tablet has a diameter of 10 mm and a weight of about 360 mg for a 200 mg dose of fenofibrate.

Example 2 a) Preparation of the Internal-Phase Granules

The following are mixed for about 6 minutes in a horizontal mixer (LÖDIGE):

3.4 kg of micronized fenofibrate (mean particle diameter: 7 µm)
1.156 kg of pregelatinized starch (LYCATAB® PGS)
0.595 kg of microcrystalline cellulose (AVICEL® PH 102)

This mixture is then granulated in the mixer by spraying with a solution of 178.5 g of polyvinylpyrrolidone (KOLLIDON K 30) and 119 g of polysorbate 80 (TWEEN® 80 obtained from Uniqema) in 1.813 l of purified water. The spraying lasts about 30 min. The granules obtained are sized by passage over an oscillating granulator (ERWEKA) equipped with a grid having a mesh size of 2.5 mm. The sieved granules are then dried in a fluidized bed dryer (GLATT) with an air inlet temperature of 50-60° C.

b) Preparation of the Mixture for Compression 1.859 kg of the granules obtained by the above process, 142 g of crosslinked polyvinylpyrrolidone (reference POLYPLASDONE® XL 10, marketed by GAF) and 29 g of magnesium stearate are mixed in a horizontal paddle mixer (LÖDIGE) for 6 minutes. This gives the granules mixed with the external phase and ready for compression.

c) Preparation of the Tablets

The mixture obtained above is compressed in an alternating machine equipped with a 10R10 die. The machine is adjusted to produce tablets with a unit weight of 350 mg, which corresponds to a 200 mg dose of fenofibrate per tablet. The tablets obtained have a hardness of about 89 N.

d) Film-Coating

The tablets obtained according to the above operation are placed in a stainless steel turbine equipped with a spray gun, a hot-air blower and a suction system. The rotation of the turbine is set to 16 rpm and a solution of 12.8 g of film-forming polymer (reference OPADRY OYS®) in 243 g of 80% ethanol is sprayed in. The spraying lasts about 1 hour. The film-coated tablets obtained are then cooled and packaged. Each tablet has a diameter of 10 mm and a weight of about 360 mg for a 200 mg dose of fenofibrate.

Comparative Example

By way of comparison, a batch of fenofibrate tablets was also prepared by following a protocol conventionally used by those skilled in the art, in which the excipients constituting the internal phase of Preparation 1b of Example 1 above were replaced with 2.550 kg of lactose, 952 g of sodium carboxymethyl starch and 595 g of microcrystalline cellulose, and using 238 g of PVP XL10 and 170 g of magnesium stearate as the excipients of the external phase of Preparation 1c, the compression and film-coating being carried out analogously to the manufacturing process of Example 1 with a 200 mg dose of fenofibrate for a 360 mg film-coated tablet. The tablets obtained have a hardness of about 72 to 75 N.

Pharmacokinetic Study

The tablets according to Example 1 of the invention and the tablets obtained according to the Comparative Example were evaluated from a pharmacokinetic point of view during clinical studies on healthy humans.

The first study was conducted on 6 subjects in order to compare LIPANTHYL® 200M gelatin capsules (formulation marketed in France) with the tablets obtained according to the Comparative Example. The treatment was administered orally 30 min after breakfast and the efficacy of the treatment was evaluated by assay of the serum fenofibric acid level as a function of time. From these measurements it was possible to calculate the area under the curve ($AUC_{0-\infty}$), the maximum concentration attained ($C_{max}$), the time corresponding to this maximum concentration ($T_{max}$) and the half-life of the product ($T_{1/2}$). The results obtained are collated in the Table below:

TABLE I

|  | $AUC_{0-\infty}$ (µg/ml · h) | $C_{max}$ (µg/ml) | $T_{max}$ (hours) | $T_{1/2}$ (hours) |
|---|---|---|---|---|
| Comparative tablet | 102.7 | 5.36 | 4.2 | 20.3 |
| LIPANTHYL 200M | 137.2 | 8.50 | 4.7 | 18.7 |
| CI 90% log ½ | 0.63-0.88 | 0.53-0.74 | — | — |
| Conclusion | not bioequivalent | not bioequivalent | — | — |

CI is the confidence interval.

This first study shows that the tablet according to the Comparative Example, although comprising the same amount of fenofibrate, is not bioequivalent to the LIPANTHYL® 200M gelatin capsule and has an inferior bioavailability.

The second study, conducted on 9 subjects under conditions analogous to the previous study, enabled the tablet of Example 1 according to the invention to be compared with the LIPANTHYL® 200M gelatin capsule. The results are collated in Table II below:

TABLE II

|  | $AUC_{0-t}$ (µg/ml · h) | $C_{max}$ (µg/ml) | $T_{max}$ (hours) | $T_{1/2}$ (hours) |
|---|---|---|---|---|
| LIPANTHYL® 200M | 113.8 | 6.97 | 3.9 | 19.90 |
| Tablet of Example 1 | 115.1 | 6.86 | 4.5 | 18.4 |
| CI 90% 2/1 | 0.95-1.08 | ANOVA NS | | |
| Conclusion | 1 and 2 bioequivalent | | — | — | t: time of the last quantifiable point

These results show very similar values for the 2 galenic forms, indicating that these two formulations, each containing 200 mg of fenofibrate, are bioequivalent.

The tablets obtained according to Examples 1 and 2 according to the invention were compared from the point of view of their dissolution rate. This test was performed on the non-film-coated tablets by measuring the amount of fenofibrate dissolved as a function of time in a 0.02 M solution of sodium laurylsulfate placed in a Dissolutest apparatus, at a temperature of 37° C. and with the stirrer speed set to 100 rpm; using this protocol, the tablets obtained according to Examples 1 and 2 show the dissolution profiles collated in Table III (the results are expressed as the percentage of fenofibrate dissolved, calculated relative to the total amount contained in the tablet):

TABLE III

| Time (min) | Example 1 | Example 2 |
|---|---|---|
| 0 | 0 | 0 |
| 10 | 37.1 | 44.8 |
| 20 | 63.1 | 69.1 |
| 30 | 74.1 | 77.5 |
| 40 | 79.6 | 82.6 |
| 50 | 83.9 | 85.6 |
| 60 | 86.2 | 88.1 |

The values obtained show totally similar dissolution profiles, indicating that the two tablets are equivalent.

The tablets according to the invention therefore make it possible to obtain a treatment efficacy equivalent to that of LIPANTHYL® 200M gelatin capsules, with the advantages of dispensing with the presence of gelatin in the gelatin capsule, providing a more compact dosage unit that is easier to swallow, and finally allowing a greater production rate than that of gelatin capsules.

These tablets can be used analogously to LIPANTHYL® 200M gelatin capsules for the treatment of hypercholesterolemia and hypertriglyceridemia.

The invention claimed is:

1. A fenofibrate tablet consisting of:
   crosslinked polyvinylpyrrolidone;
   50 to 250 mg micronized fenofibrate; and
   a lubricant;
   wherein the fenofibrate is in granules, the granules consisting of:
      the micronized fenofibrate;
      a surfactant in an amount of 1 to 5% the weight of the fenofibrate;
      polyvinylpyrrolidone,
      a pregelatinized starch in an amount of 15 to 40% the weight of the fenofibrate; and
      a microcrystalline cellulose in an amount of 5 to 30% of the weight of the fenofibrate;
   wherein the tablet comprises greater than 50% by weight fenofibrate.

2. The tablet of claim 1, wherein the surfactant is solid and is comicronized with the fenofibrate.

3. The tablet of claim 1, comprising 200 mg of fenofibrate and weighing less than 400 mg.

4. The tablet of claim 1, wherein the surfactant is sodium laurylsulfate.

5. The tablet of claim 1, wherein the polyvinylpyrrolidone has an average molecular weight in the order of 25,000 to 100,000.

6. The tablet of claim 1, wherein the crosslinked polyvinylpyrrolidone is present in an amount of 6 to 18% of the weight of the fenofibrate.

7. The tablet of claim 6, wherein the crosslinked polyvinylpyrrolidone is present in an amount of 10 to 14% of the weight of the fenofibrate.

8. The tablet of claim 5, which is a coated tablet.

9. A fenofibrate tablet consisting of:
   crosslinked polyvinylpyrrolidone;
   50 to 250 mg micronized fenofibrate;
   a lubricant; and
   a flow aid;
   wherein the fenofibrate is in granules, the granules consisting of:
      the micronized fenofibrate,
      a surfactant in an amount of 1 to 5% the weight of the fenofibrate,
      polyvinylpyrrolidone,
      a pregelatinized starch in an amount of 15 to 40% the weight of the fenofibrate, and
      a microcrystalline cellulose in an amount of 5 to 30% of the weight of the fenofibrate;
   wherein the tablet comprises greater than 50% by weight fenofibrate.

10. The tablet of claim 9, wherein the surfactant is solid and is comicronized with the fenofibrate.

11. The tablet of claim 9, comprising 200 mg of fenofibrate and weighing less than 400 mg.

12. The tablet of claim 9, wherein the surfactant is sodium laurylsulfate.

13. The tablet of claim 9, wherein the polyvinylpyrrolidone has an average molecular weight in the order of 25,000 to 100,000.

14. The tablet of claim 9, wherein the crosslinked polyvinylpyrrolidone is present in an amount of 6 to 18% of the weight of the fenofibrate.

15. The tablet of claim 9, wherein the crosslinked polyvinylpyrrolidone is present in an amount of 10 to 14% of the weight of the fenofibrate.

16. The tablet of claim 9, which is a coated tablet.

17. Fenofibrate granules consisting of:
   micronized fenofibrate,
   a surfactant in an amount of 1 to 5% the weight of the fenofibrate,
   polyvinylpyrrolidone,
   a pregelatinized starch in an amount of 15 to 40% the weight of the fenofibrate, and
   a microcrystalline cellulose in an amount of 5 to 30% of the weight of the fenofibrate.

18. Fenofibrate granules of claim 17, wherein the surfactant is solid and is comicronized with the fenofibrate.

19. Fenofibrate granules of claim 17, wherein the surfactant is sodium laurylsulfate.

20. Fenofibrate granules of claim 17, obtainable by a process comprising:
   the comicronization of fenofibrate and a solid surfactant in an amount of 1 to 5% the weight of the fenofibrate;
   the mixing, in the form of powders, of the resulting product with pregelatinized starch in an amount of 15 to 40% the weight of the fenofibrate, and with microcrystalline cellulose in an amount of 5 to 30% of the weight of the fenofibrate;
   the granulation of the resulting mixture of powders with an aqueous solution of polyvinylpyrrolidone.

21. Fenofibrate granules of claim 17, obtainable by a process comprising:
   the mixing, in the form of powders, of micronized fenofibrate with pregelatinized starch in an amount of 15 to 40% the weight of the fenofibrate, and with microcrystalline cellulose in an amount of 5 to 30% of the weight of the fenofibrate;
   the granulation of the resulting mixture of powders with an aqueous solution of polyvinylpyrrolidone and with a surfactant in an amount of 1 to 5% the weight of the fenofibrate.

* * * * *